United States Patent [19]
Kashmer

[11] Patent Number: 6,165,153
[45] Date of Patent: *Dec. 26, 2000

[54] SINGLE USE SYRINGE DEVICE

[75] Inventor: James S. Kashmer, Andover, N.J.

[73] Assignee: SafeGard Medical Limited, Monaco

[ * ] Notice: This patent is subject to a terminal disclaimer.

[21] Appl. No.: 09/170,384

[22] Filed: Oct. 13, 1998

[51] Int. Cl.[7] .................................................. A61M 5/00
[52] U.S. Cl. ........................ 604/110; 604/218; 604/220
[58] Field of Search .................................. 604/220, 218, 604/110, 187, 263, 192

[56] References Cited

U.S. PATENT DOCUMENTS

| | | | |
|---|---|---|---|
| 4,233,975 | 11/1980 | Yerman | 604/110 |
| 4,846,801 | 7/1989 | Okuda et al. | 604/218 |
| 5,045,063 | 9/1991 | Spielberg | 604/110 |
| 5,106,371 | 4/1992 | Zhao et al. | 604/110 |
| 5,135,495 | 8/1992 | Arcusin | 604/220 X |
| 5,259,840 | 11/1993 | Boris | 604/218 X |
| 5,484,413 | 1/1996 | Gevorgian | 604/220 X |

*Primary Examiner*—John D. Yasko
*Attorney, Agent, or Firm*—Choate, Hall & Stewart

[57] ABSTRACT

A single-use syringe assembly is provided and includes an elongated syringe barrel with a plunger assembly disposed therein. The plunger assembly includes an elongated plunger rod having a plunger tip located distally. The plunger tip contains a locking detent disposed a the distal end of the tip. The syringe barrel has a nozzle at the substantially closed distal end, the nozzle adapted to conform to the plunger tip. The distal end of the nozzle contains an annular inward biased ring adapted to mate with the locking detent of the plunger tip. Upon usage of the syringe and application of force to apply the liquid, the locking detent is irreversibly mated with the nozzle inwardly biased ring, thereby preventing reuse of the syringe assembly.

36 Claims, 15 Drawing Sheets

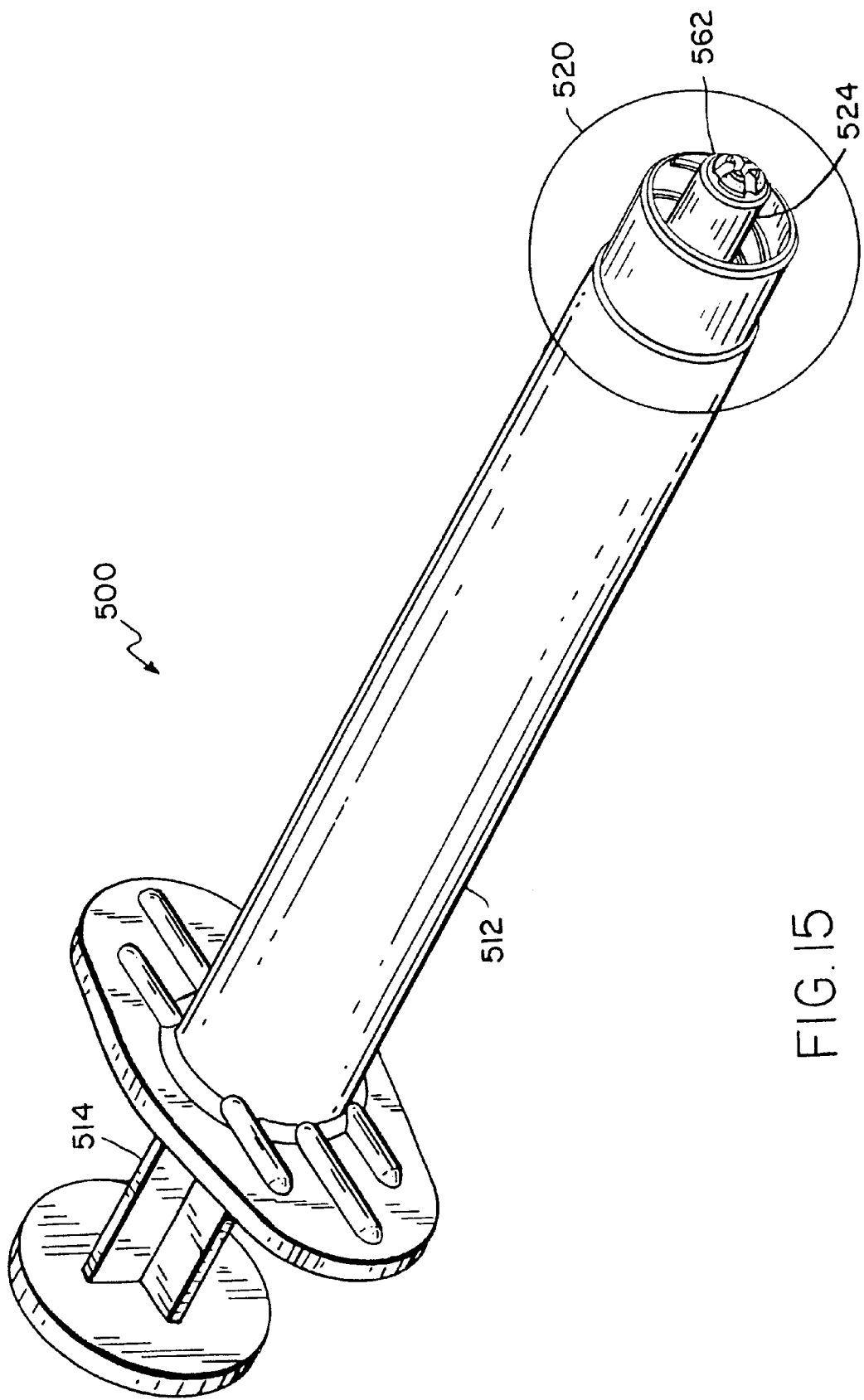

SINGLE USE SYRINGE DEVICE

BACKGROUND OF THE INVENTION

This invention relates generally to a single use syringe device and more specifically to a syringe device having an integral locking mechanism to prevent extraction of the plunger after use.

The increasing awareness of the importance of sterility in hypodermic devices has led to the advent of disposable syringes. The initial sterility, coupled with their low cost, has led to the widespread use of these devices in preference over reusable devices requiring sterilization before reuse. But the widespread use of disposable syringes has created problems. By their economic nature, inexpensive devices, utilized in high numbers, tend to make inventory controls on new and used devices difficult and prone to breakdown It is not uncommon for syringes, along with the attached needles, to find their way into unauthorized hands. Once control is lost, these devices may be reused without sterilization.

Reuse of hypodermic syringes, intended for a single use only, is instrumental in the transfer of contagious diseases and facilitation of drug abuse. Intravenous drug users who routinely share and reuse syringes are a high risk group with respect to the HIV and hepatitis virii. Easy access to the devices further facilitates illegal drug use. In addition, the effects of repeated uses of syringe products may be responsible for the spread of many other diseases.

One solution to these problems is to develop syringes which functionally self-destruct after a single application. While non-reusable syringes will not necessarily stop illegal drug use, it can prevent sharing of contaminated hypodermic syringes and thus help reduce the spread of diseases.

Many approaches have been made to prevent and limit reuse. Initially, syringe designs incorporated features facilitating an explicit destructive act. Thus, by the application of force, the syringe becomes inoperable. Other designs included special structures to lock the device in a position preventing reuse. Some designs utilized locks incorporated in the barrel section of the syringe, requiring full extension to engage the device. Other designs require the syringe to be prefilled, and may not be filled in the conventional manner. Additional designs require multiple parts and careful assembly.

The ideal syringe design would incorporate a locking mechanism that would allow conventional use of the syringe (i.e. normal filling operations). In addition, the design would be simple to operate, not requiring any special training. The design should be able to utilize standard hypodermic needles. The design should be inexpensive and reliable. Finally, the design should encourage the full and complete elimination of valuable medication.

SUMMARY OF THE INVENTION

Thus, it is an object of the invention to provide a single-use syringe incorporating a locking mechanism preventing reuse.

It is an object of the invention to provide a single-use syringe that performs much like a conventional disposable syringe.

It is an additional object of the invention to provide a single-use syringe capable of using conventional hypodermic needles.

It is a further object of the invention to provide a single-use syringe that is simple and inexpensive.

It is also an object of the invention to provide a hypodermic syringe that does not waste medications.

In the present invention, the plunger is adapted to included a locking pin extending longitudinally from the piston portion of the plunger. The locking pin is adapted to include at least one detent. The piston is adapted to surround at least a portion of the locking pin, allowing the locking pin to protrude through the plunger sufficiently to expose the detent. The syringe barrel includes a port at the cap end. The port is adapted to mate with the locking pin and includes a fustrum or annular portion biased in toward the locking pin. The fustrum or annular portion is adapted to mate with the detent when the plunger is fully compressed, thereby locking the plunger and piston in place and preventing the extension of plunger thus preventing reuse. In addition, the mating between the port and the locking pin reduces the dead space in the used syringe, thus reducing the amount of materials left in the syringe after use.

The above mentioned objectives of the present invention will become more apparent and the invention itself better understood with reference to the following description of the embodiments of the present invention in conjunction with the accompanying drawings.

BRIEF DESCRIPTION OF THE DRAWINGS

The foregoing and other objects, features, and advantages of the present invention will become more apparent from the following detailed description of the preferred embodiment of the invention as illustrated in the accompanying drawings wherein:

FIGS. 15 is an isometric view of the sixth embodiment of the present invention with the plunger in the locked position.

DETAILED DESCRIPTION OF THE PREFERRED EMBODIMENT

Figure 1:
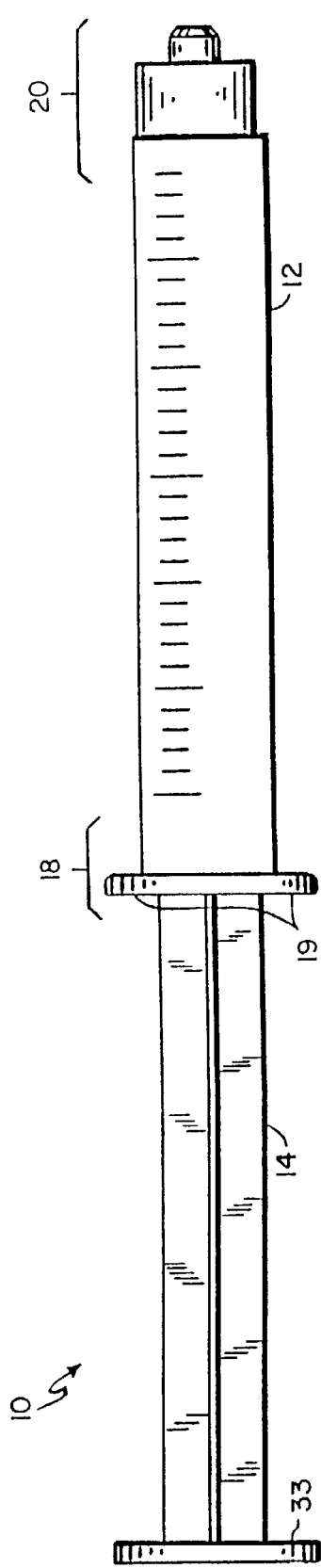
FIGS. 1, 1A and 1B are side and cross-sectional views of a first embodiment of the present invention with the plunger in the retracted position.

The embodiments of the present inventions shown in the drawings, the single-use syringe of the present invention, consists of a syringe assembly comprising a hollow elongate inner syringe barrel with an elongate plunger assembly reciprocally received therein. In the description below, the terms "distal" or "distal end" are used herein to define the part or surface of an element which is facing the patient or positioned furtherest from the user of the syringe as described hereinafter. The terms "proximal" or "proximal end" are used herein to define the part or surface of an element which is facing away from the patient or positioned closest to the user.

Figure 1A:
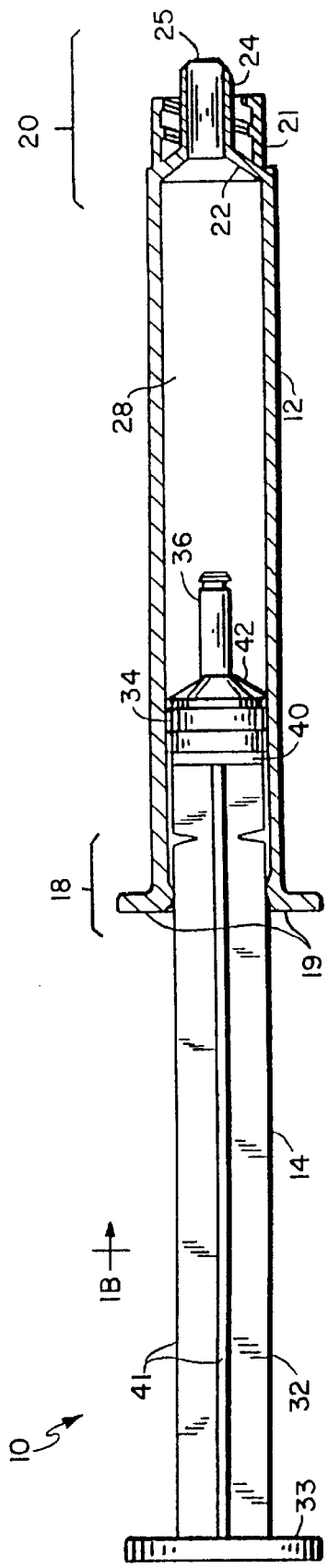
Figure 1B:
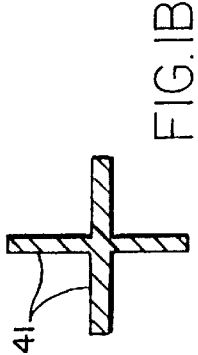

The first embodiment of the present invention is illustrated in FIGS. 1 through 6 with FIG. 9 illustrating the operation of an aspect of the embodiment. Turning to FIGS. 1, 1A and 1B, the syringe assembly includes a syringe barrel 12 consisting of an elongated tubular member having an open proximal end 18 with a pair of radially extending finger members 19 thereon. Extending finger members 19 are sized so as to facilitate compression of the plunger assembly 14 into syringe barrel 12 during application by the user. Syringe barrel 12 also includes a partially closed or reduced diameter distal end 20. The inner surface of the distal end 20 has a tapered and reduced diameter section forming shoulder area 22 to adjacently receive the distal end of the plunger assembly 14.

Figure 6:
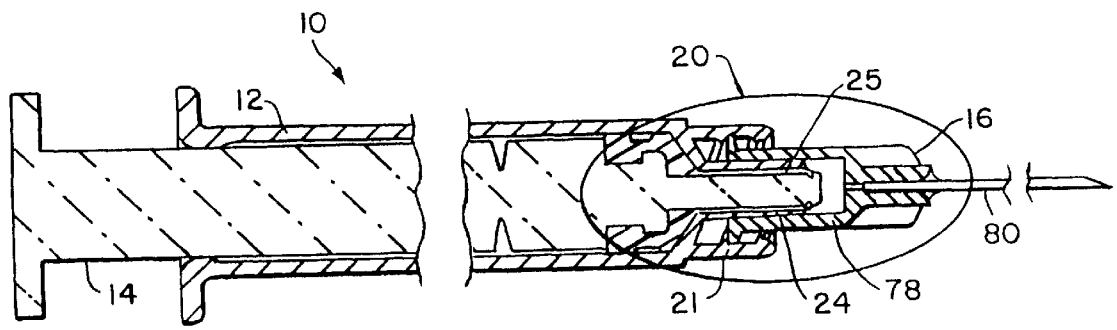
FIGS. 6 and 6A are cross-sectional views of a first embodiment of the present invention of FIG. 1 illustrating the placement of a locked plunger with respect to a needle mounted on the syringe.
Figure 6A:
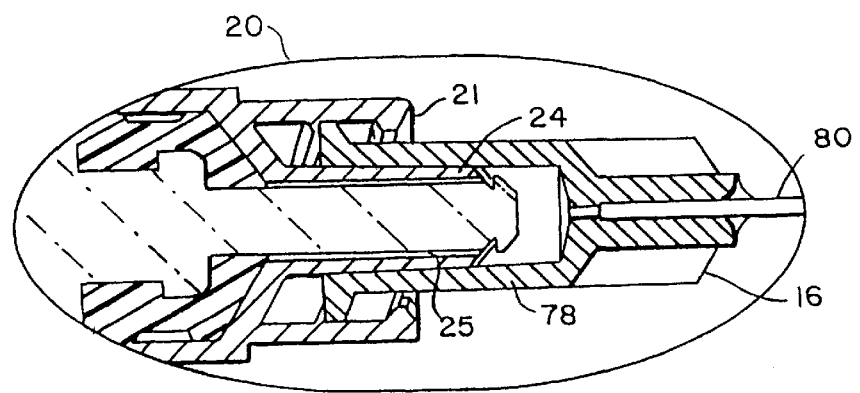

The distal end 20 of barrel 12 further includes a needle mount 21 which is adapted to receive a needle assembly mounted thereon. The needle mount 21 may comprise a Luer lock or Luer slip fitting. Within needle mount 21 is a nozzle 24 including a nozzle lumen or port 25 therein to provide fluid communication between the syringe barrel 12 and needle assembly. FIGS. 6 and 6A illustrate the needle mount 21 when mated with a needle assembly 16. The needle assembly 16 includes a needle hub 78 attached to a needle cannula 80. As illustrated, the needle hub 78 mates to the needle mount 21, with nozzle 24 disposed internal to needle hub 78.

With reference to FIG. 1A, the plunger assembly 14 of the preferred embodiment of the present invention includes an elongate plunger rod 32 and an elastomeric piston member 34. The proximal portion of the plunger rod 32 connects to an enlarged head portion 33 designed to be grasped or pushed by the user's thumb. The distal portion of the plunger rod 32 connects to a circular end member 40, which further leads to a tapered plunger tip 36 having a generally circular cross section. FIG. 1B illustrates how the plunger rod 32 may be formed by a plurality of radially extending rib members 41 that longitudinally extend between head portion 33 and circular end member 40.

Figure 2:
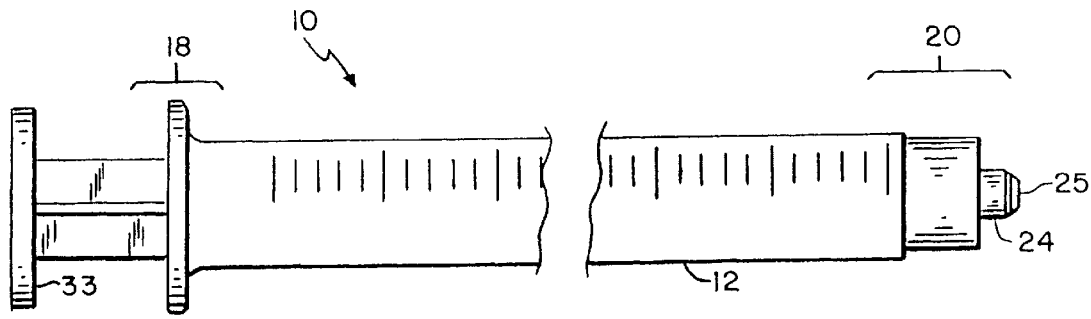
FIGS. 2, 2A and 2B are side and cross-sectional views of a first embodiment of the present invention with the plunger in the start of resistance position.
Figure 2A:
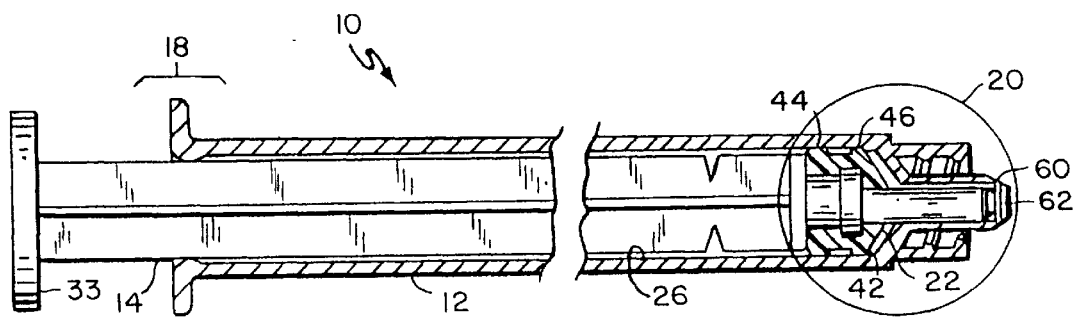
Figure 2B:
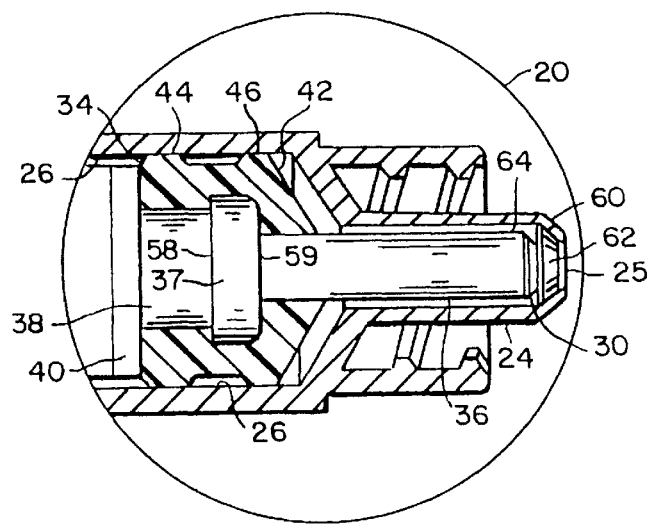

Elastomeric piston member 34 is joined to the distal portion of plunger rod 32 via a structure illustrated in FIG. 2B. First, a reduced diameter neck portion 38 extends distally from the circular end member 40. Connected to the neck portion 38 is a cylindrical lip member 37 having a diameter greater than neck portion 38. The proximal surface 58 of the cylindrical lip member 37 is substantially perpendicular to neck portion 38 so as to facilitate retention of the elastomeric piston member 34. The distal surface 59 of cylindrical lip member 37 is shaped to facilitate the mounting of the elastomeric piston member 34. Distally connected to the cylindrical lip member 37 is a plunger tip 36.

With reference to FIGS. 2A and 2B, the piston member 34 is a generally cylindrically-shaped member constructed of a resilient material such as butyl rubber. The distal end 42 of the piston member 34 is tapered and sized to conform to the shoulder area 22 of syringe barrel 12. FIG. 2B illustrates that the outer circumference of the piston member 34 includes distal and proximal annular lip members, 44 and 46 respectively, which provide a sealing contact with the inner surface 26 of the syringe barrel 12. As illustrated in FIG. 3B, piston member 34 includes a centrally located bore 48 extending from the proximal end through the distal end of piston member 34. The bore 48 includes a proximal first section having a radially directed piston lip 52 and central second section 54 forming a longitudinally enlarged recess area in the piston member 34. The distal surface 57 of central section 54 is oriented generally perpendicular to the piston lip 52 and designed to be parallel to the distal surface 59 of the plunger lip member 37. This structure facilitates the retention of the elastomeric piston member 34 at the distal end of the plunger 14. A distal third section 56 is adapted to conform to and surround a portion of plunger tip 36.

Turning to FIGS. 6 and 6A, the outer surface of the distal end 20 of barrel 12 contains a nozzle assembly 24. As illustrated, the nozzle assembly 24 is adapted to mate with the needle assembly 16, which is formed by a needle hub 78 attached to a needle cannula 80. Thus, user application of the syringe assembly 10 causes fluids contained in a chamber 28 (defined by barrel 12 and elastomeric piston 34 as illustrated in FIG. 1A) to travel through nozzle assembly 24 to needle assembly 16 via nozzle lumen 25.

The distal end of barrel 12 and the distal end of plunger assembly 14 further include elements to form a locking mechanism to lock the plunger assembly 14 when the user or clinician has completed the delivery of medication to the patient. The distal end of nozzle lumen 25 contains an inwardly biased annular portion 60 as illustrated in FIG. 2B. The inwardly biased annular portion 60 is compliantly adapted to expand under force, such as a force directed from the proximal direction. The plunger tip 36 also contains a distally located annular detent 30 and tip cap 62. The annular detent is adapted to mate with the biased annular portion 60 of nozzle 24. The annular detent 30 is formed at the distal end of plunger tip 36, and divides the tip into a cylindrical tip section 64 and a tip cap 62. The annular detent 30 is formed by a tapering of tip section 64.

Operation of the Syringe

FIGS. 2 and 2B illustrate the preferred embodiment of the present invention in its likely packaged postion, here illustrated as the start of resistance position. In this position, syringe assembly 10 is in the unlocked state, ready to be mated to a needle assembly 16 and filled with fluid. (While the diagrams illustrate only the syringe assembly it is understood by one of ordinary skill in the art that the following operation would occur while the syringe assembly 10 was mated to the appropriate equipment.)

The user fills the syringe assembly 10 with fluid as with a conventional non-locking disposable syringe. The plunger assembly 14 is drawn or pulled proximally from the barrel 12, thereby filling the chamber 28, formed in the space bounded by the elastomeric piston assembly 34 and the barrel 12, with air. FIGS. 1 and 1A illustrate the syringe assembly as it would appear upon filling the chamber with either air or fluid. The syringe assembly 10, mated with needle assembly 16, may now be joined to a vial containing the fluid. The plunger assembly is now partially compressed to force air from the syringe assembly into the vial so as to pressurize the vial. This is necessary, as otherwise the drawing of the fluid from the vial would ultimately create a back-vacuum and prevent drawing of fluid. The plunger assembly 14 is then drawn or pulled proximally from the barrel 12, thereby causing a vacuum in the chamber to form in the chamber 28, formed in the space bounded by the elastomeric piston assembly 34 and the barrel 12. The vacuum causes fluid to be drawn into the chamber via the nozzle lumen 25. FIGS. 1 and 1A illustrate the syringe assembly 10 in the filled and unlocked state. In this state, the syringe is ready to be applied to the patient.

Application is accomplished by compressing the plunger assembly 14 into the barrel 12, thereby forcing the fluid in chamber 28 through nozzle lumen 25. Initially, compression moves the plunger assembly from the filled and unlocked position to a position where the majority of the fluid has been discharged. In this first discharged stage, illustrated in FIGS. 2, 2A, and 2B the plunger tip cap 62 begins making initial contact with the inwardly biased annular nozzle ring 60 located in the distal end of the nozzle lumen 25. In this state, any additional movement of the plunger assembly in the distal direction requires an increase in the force applied by the user. Thus, the user receives feedback from the syringe assembly 10, here indicating that the plunger has reached the position where the majority of the fluid in chamber 28 has been discharged. The user now knows that additional application of force on the plunger assembly will cause the plunger assembly to ultimately enter the locked state. This increased resistance also allows the clinician to use the syringe assembly 10 to pressurize the vial (as described above) without inadvertently locking the syringe. It also allows assembly and shipping of syringe assembly 10 without accidental locking.

Figure 3:
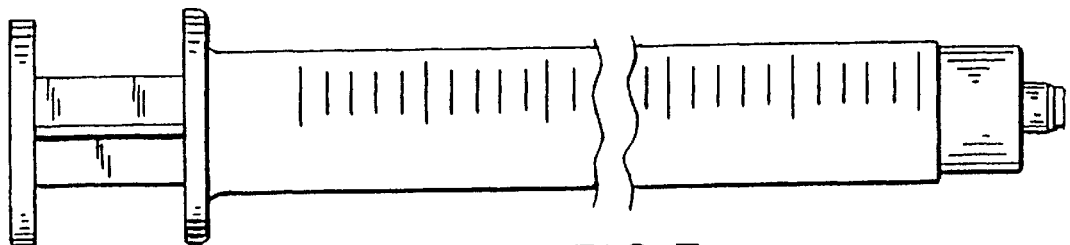
FIGS. 3, 3A and 3B are side and cross-sectional views of a first embodiment of the present invention with the plunger in the one-third engagement position.
Figure 3A:
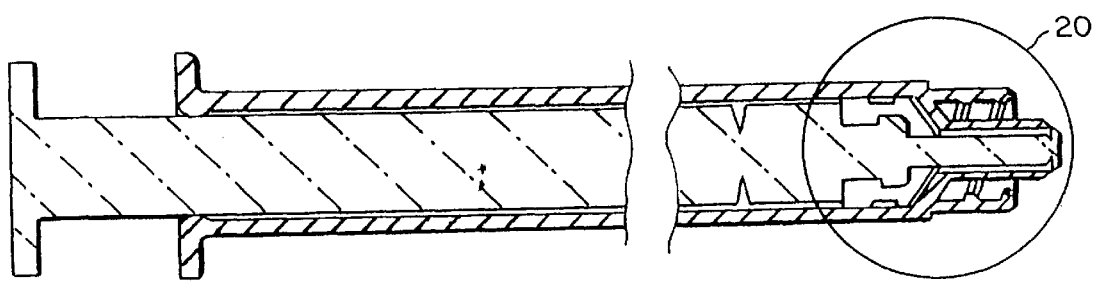
Figure 3B:
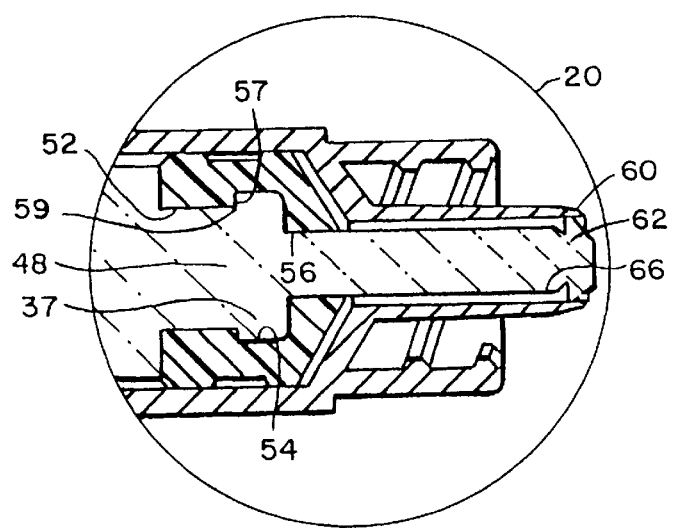

As the user increases the force applied to the plunger assembly 14, the plunger assembly continues movement as illustrated by FIGS. 3, 3A and 3B. In this position, the plunger tip cap 62 is reversing the inward bias of the biased annular nozzle ring 60, causing the annular nozzle ring 60 to move away from the plunger tip cap 62, allowing passage through.

Figure 4:
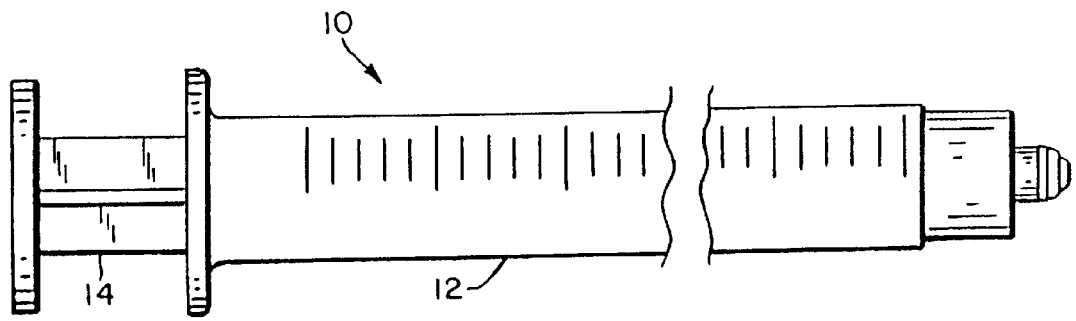
FIGS. 4, 4A and 4B are side and cross-sectional views of a first embodiment of the present invention with the plunger in the two-thirds engagement position.
Figure 4A:
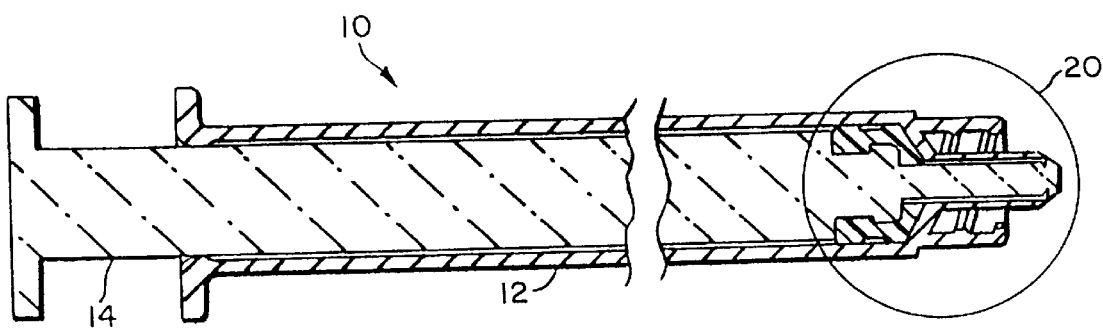
Figure 4B:
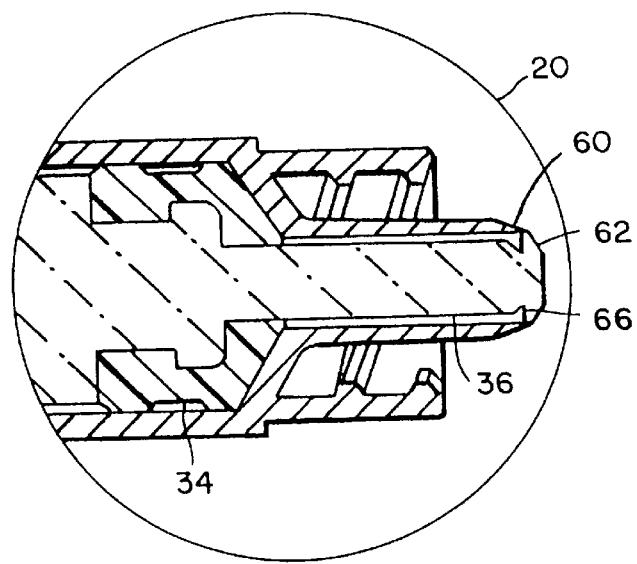

As the plunger assembly 14 continues to move distally, a point is reached where further movement requires compression of the piston member 34. FIGS. 4, 4A and 4B illustrate this point occurring where the plunger assembly has moved two thirds of the way into the locked this position, as measured from the point of increased resistance. As understood by one of ordinary skill in the art, this position may be selected by the designer via appropriate sizing of the plunger tip 36 and piston member 34. In fact, one extreme would require no compression of the piston member 34, thus allowing the plunger to enter the locked position with little increased force, locking automatically when the syringe assembly 10 is empty, thereby taking the decision lock away from clinician.

Figure 5:
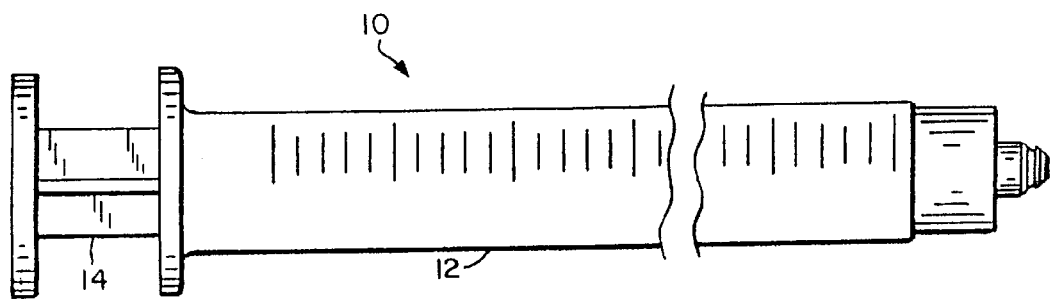
FIGS. 5, 5A and 5B are side and cross-sectional views of a first embodiment of the present invention with the plunger in the locked position.
Figure 5A:
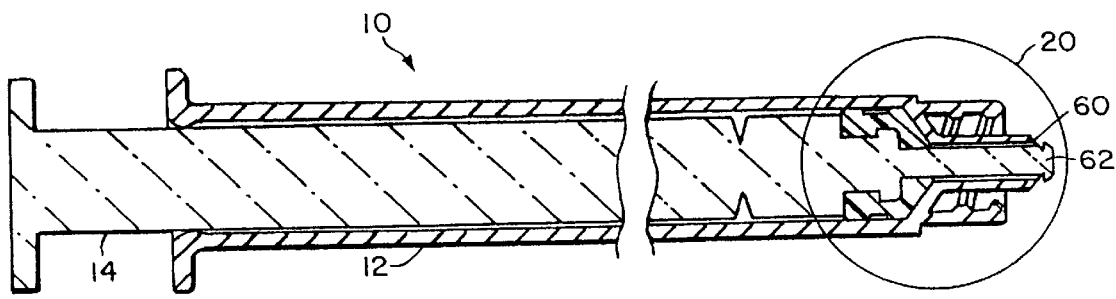
Figure 5B:
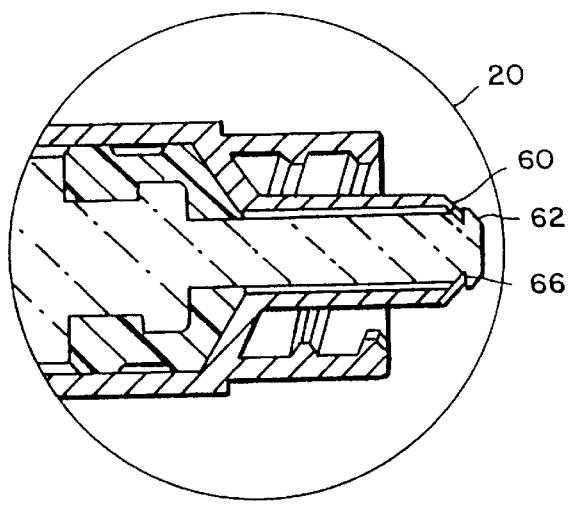

Finally, as illustrated in FIGS. 5, 5A and 5B, continued movement of the plunger assembly 14 causes it to move into the locked state. In this position, the plunger tip cap 62 has moved past the biased annular nozzle ring 60, which substantially returns to the initial inward bias. In this position, the annular nozzle ring cooperatively mates with the inner diameter section 66 of plunger tip 36. In the preferred embodiment, the return by the annular nozzle ring to the biased inward position should cause a "click" which may be heard and felt by the user. Once again the syringe assembly 10 provides feedback to the user, in this situation indicating that the syringe is in the third, empty and locked, state.

FIGS. 6 and 6A illustrate the syringe assembly 10 in the locked state, mated with a needle assembly 16. As illustrated, the plunger tip 36 substantially occupies the nozzle lumen ensuring efficient application and usage of the fluids by the user through the minimization of "dead space."

Figure 9A:
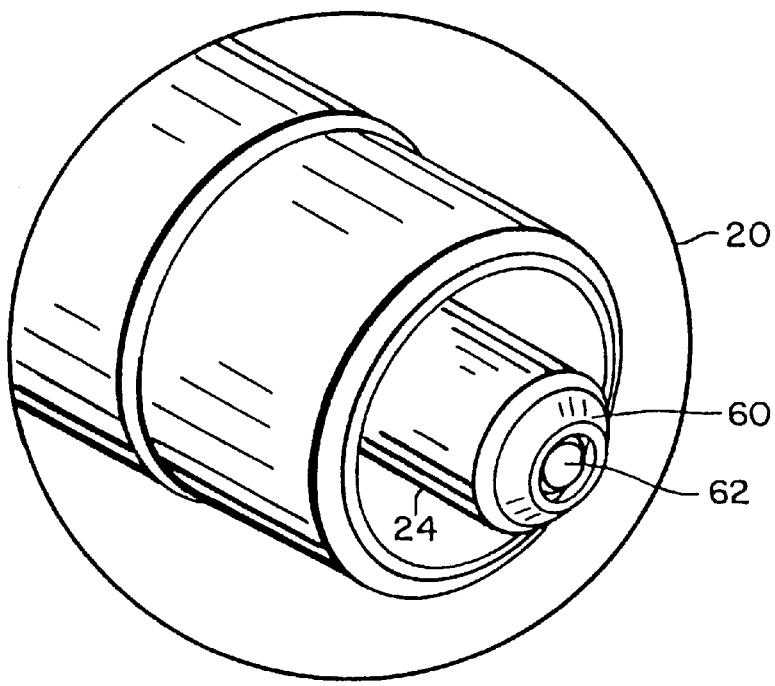
FIGS. 9A, 9B, 9C and 9D are isometric views of the distal end of the first embodiment of the present invention illustrating the transition of the plunger tip into the locked position.
Figure 9B:
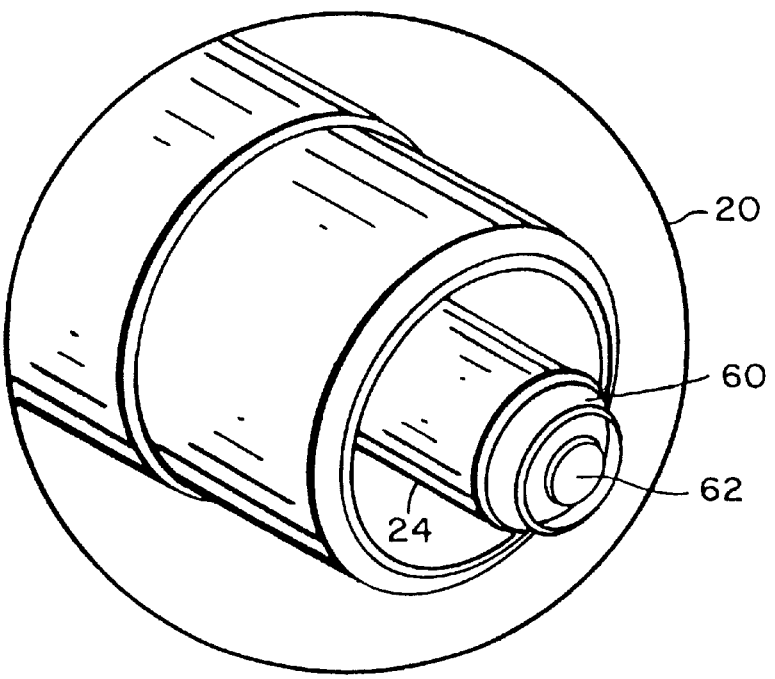
Figure 9C:
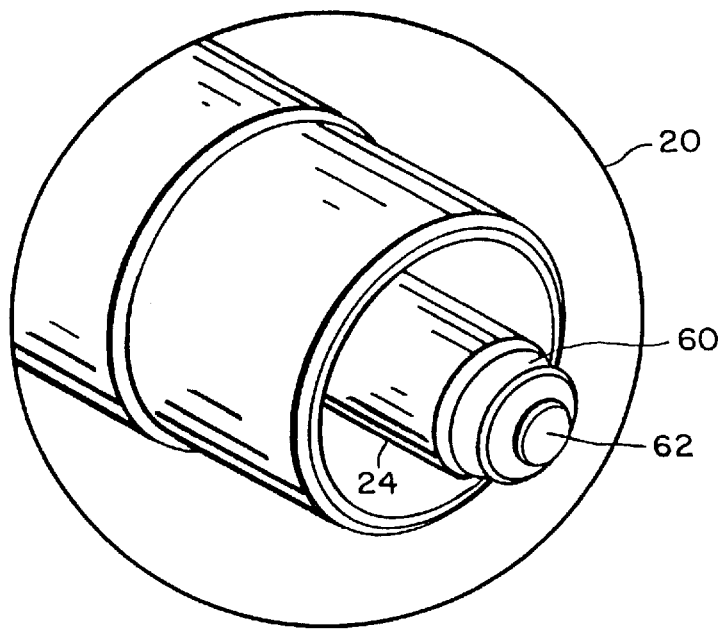
Figure 9D:
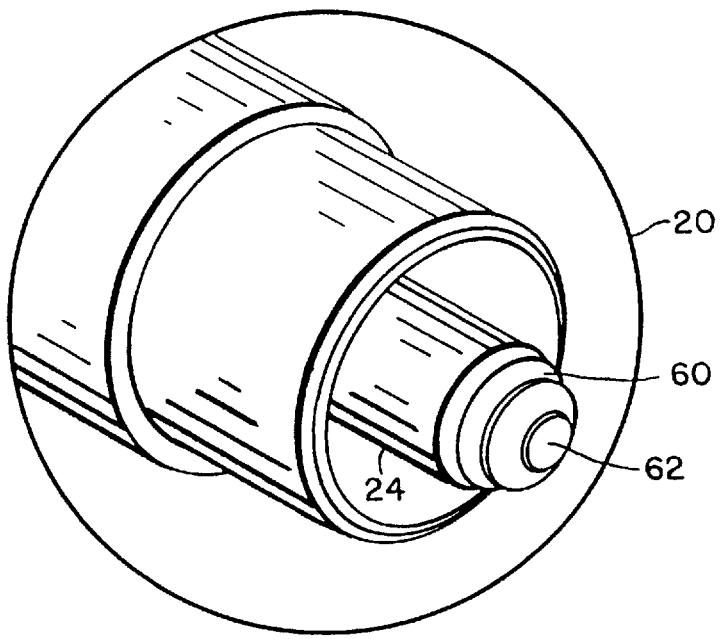

FIGS. 9A, 9B, 9C, and 9D illustrate the locking mechanism as it make the transition into the locked state. FIG. 9A is the point of initial engagement, where the clinician encounters increased resistance. FIG. 9B is the one third of the transition position. FIG. 9C is the two thirds engagement position, the point in this embodiment where the piston member bottom out and begins compression. FIG. 9D illustrates the final state where the plunger assembly 14 is locked within the syringe barrel 12.

Figure 7:
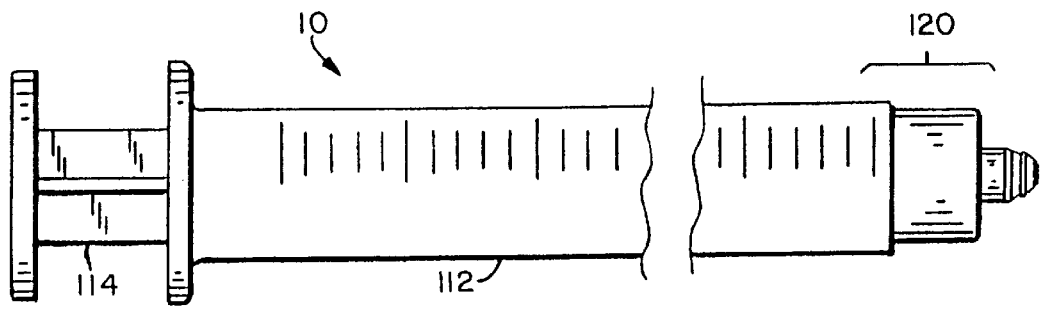
FIGS. 7, 7A and 7B are side and cross-sectional views of a second embodiment of the present invention with the plunger in the locked position.
Figure 7A:
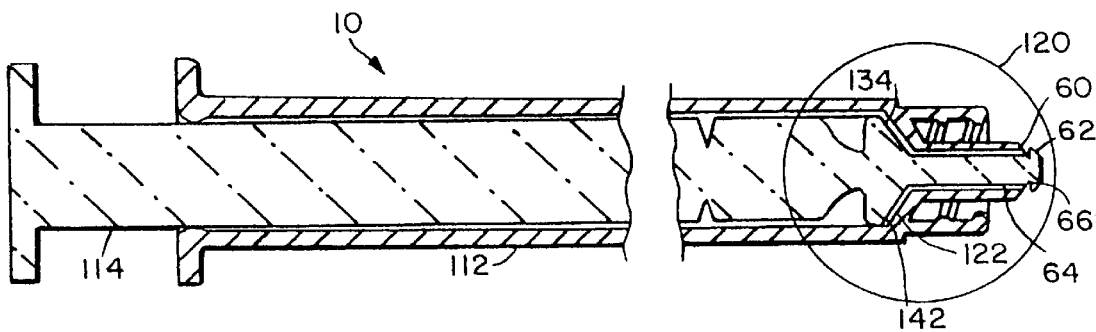
Figure 7B:
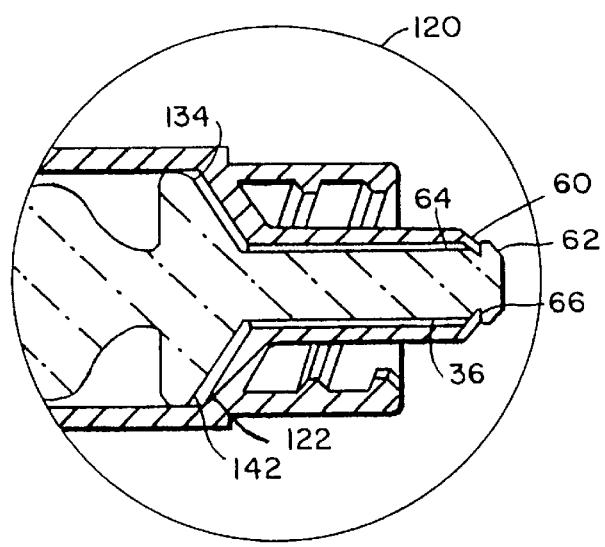
Figure 8:
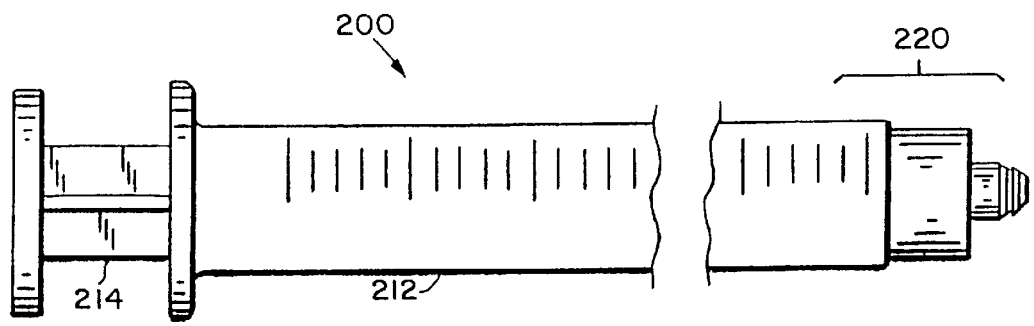
FIGS. 8, 8A and 8B are side and cross-sectional views of a third embodiment of the present invention with the plunger in the locked position.
Figure 8A:
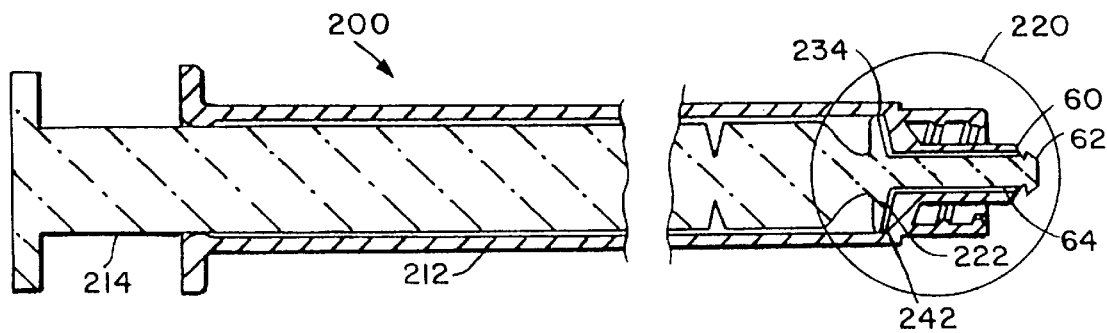

Further variations are possible on this design, such as those found in FIGS. 7A and 8A. FIGS. 7, 7A and 7B illustrate a syringe assembly 100 consisting of a plunger assembly 114 and barrel assembly 112. This embodiment differs in that the piston member 134 is integrally molded into plunger assembly 114, whose distal surface 142 is designed to mate with shoulder area 122. The locking mechanism is otherwise the same, consisting of the plunger tip cap 62 moving past the biased annular nozzle ring 60, which substantially returns to the initial inward bias mating with inner diameter section 66. As illustrated, the annular nozzle ring is cooperatively mated with the inner diameter section 66 of plunger tip 36.

Figure 8B:
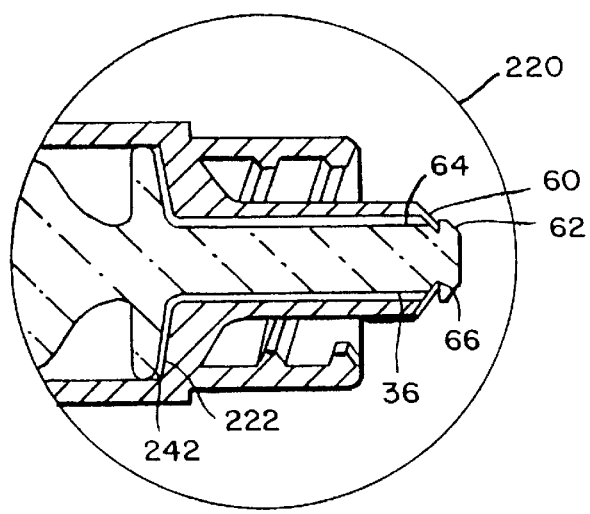

FIGS. 8, 8A and 8B illustrate an additional embodiment, with syringe assembly 200 consisting of a plunger assembly 214 and barrel assembly 212. This embodiment differs in that the piston member 234 is integrally molded into plunger assembly 214, whose distal surface 242 is designed to mate with shoulder area 222 and is substantially flat. The locking mechanism is sized appropriately for piston assembly 234.

Figure 10:
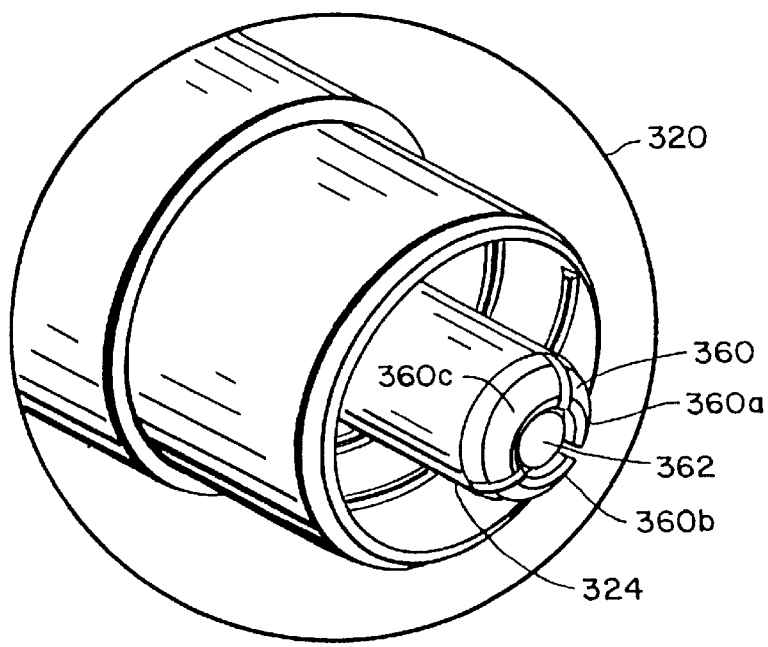
FIG. 10 is an isometric view of a fourth embodiment of the present invention with the plunger in the start of resistance position.

Variations on the locking mechanism are anticipated by the present invention. For instance, FIG. 10 illustrates the distal end 320 of an embodiment where the annular nozzle ring 360 is formed by three equivalent annular portions 360a, 360b, and 360c. The nozzle 324 and plunger tip 362 are otherwise the same as illustrated. This embodiment can be utilized to reduce the force required to move the plunger into the locked state.

Figure 11:
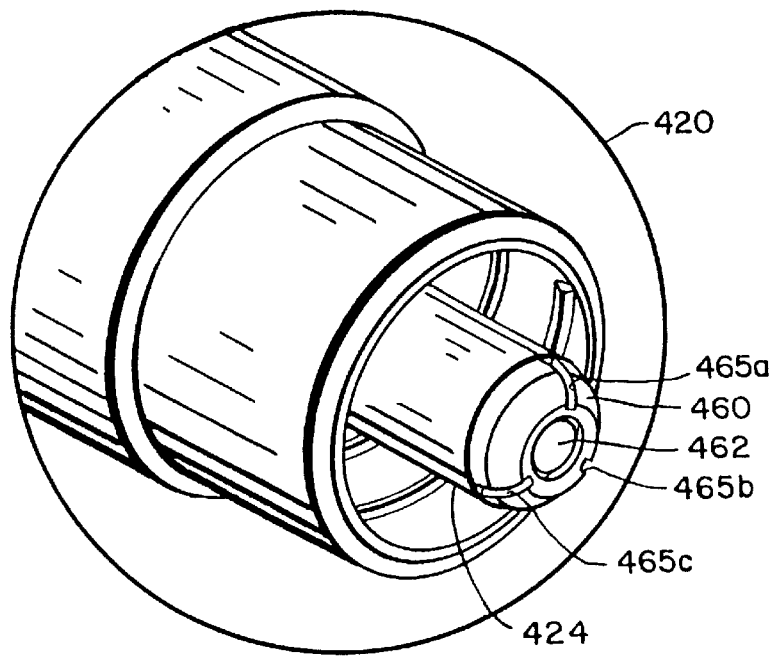
FIG. 11 is an isometric view of a fifth embodiment of the present invention with the plunger in the start of resistance position.

FIG. 11 illustrates the distal end 420 of an embodiment where the annular nozzle ring 460 is which contains three equally spaced lateral channels 465a, 465b, and 465c. The nozzle 424 and plunger tip 462 are otherwise the same as illustrated above. Again, this embodiment can be utilized to change the force required to move the plunger into the locked state.

Figure 12:
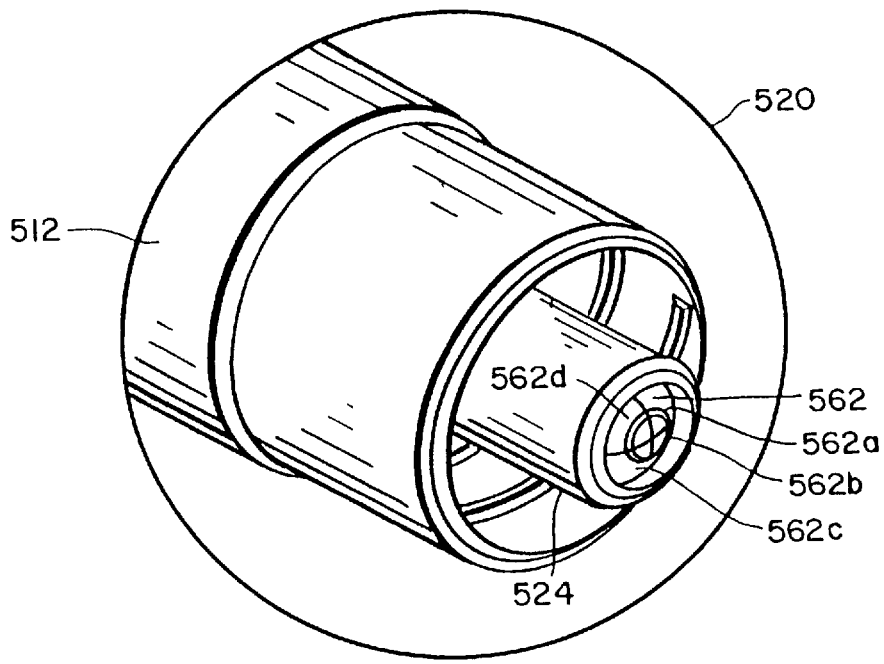
FIGS. 12 and 12A are isometric and cross-sectional views of a sixth embodiment of the present invention with the plunger in the pre-engagement position.
Figure 12A:
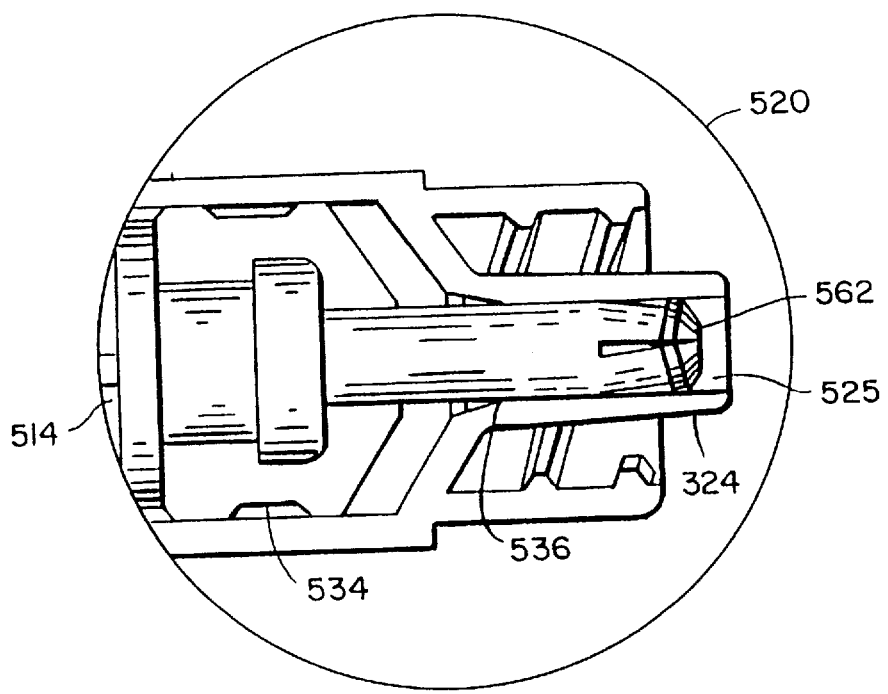

FIGS. 12–15 illustrate an embodiment for a locking plunger which may be utilized with pre-existing syringe barrel designs. Turning to FIGS. 12 and 12A, the distal end 520 of a syringe assembly utilizing a pre-existing barrel 512 and the plunger assembly 514 is illustrated. In this embodiment, the pre-existing barrel 512 contains a nozzle assembly 524. The plunger tip 536 of plunger assembly 514 is furcated. Thus, plunger tip cap 562 is divided into portions, here four portions 562a, 562b, 562c and 562d. This furcation allows the plunger tip 536 to reversibly neck down or compress, thus allowing the plunger tip 536 to travel through the pre-existing nozzle port 525. Upon transit through the nozzle port 525 the plunger tip cap reexpands, thus locking the plunger assembly into position.

Figure 13:
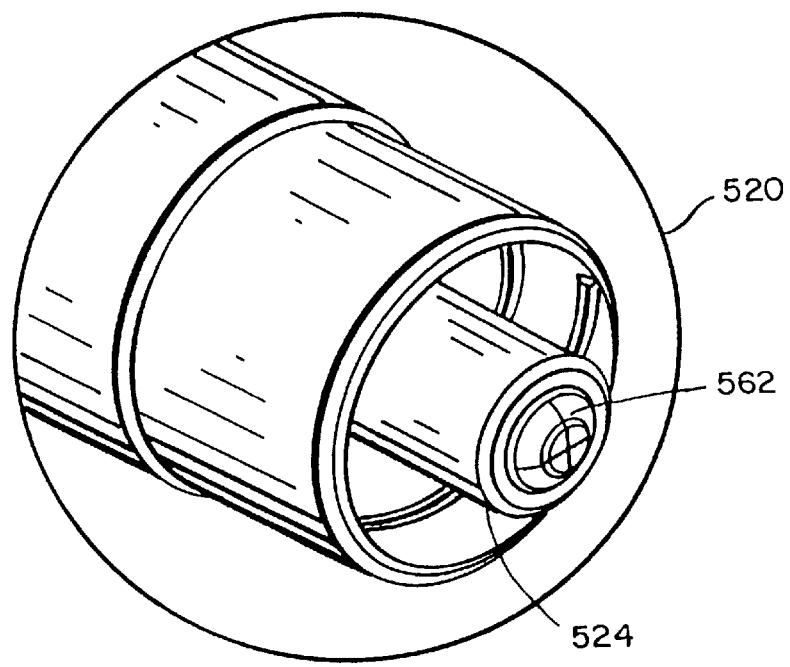
FIGS. 13 and 13A are isometric and cross-sectional views of the distal end of a sixth embodiment of the present invention with the plunger in the one-half engagement position.
Figure 13A:
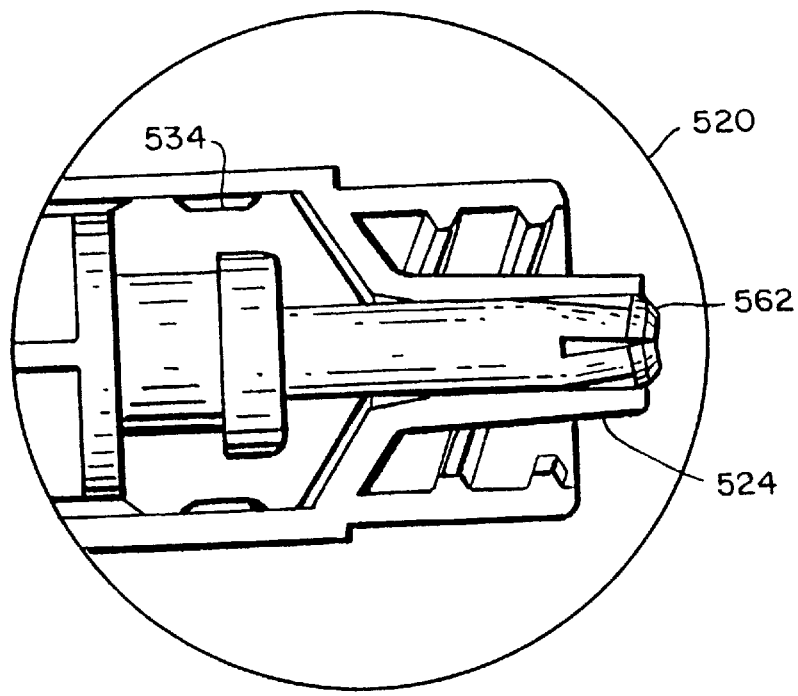
Figure 14:
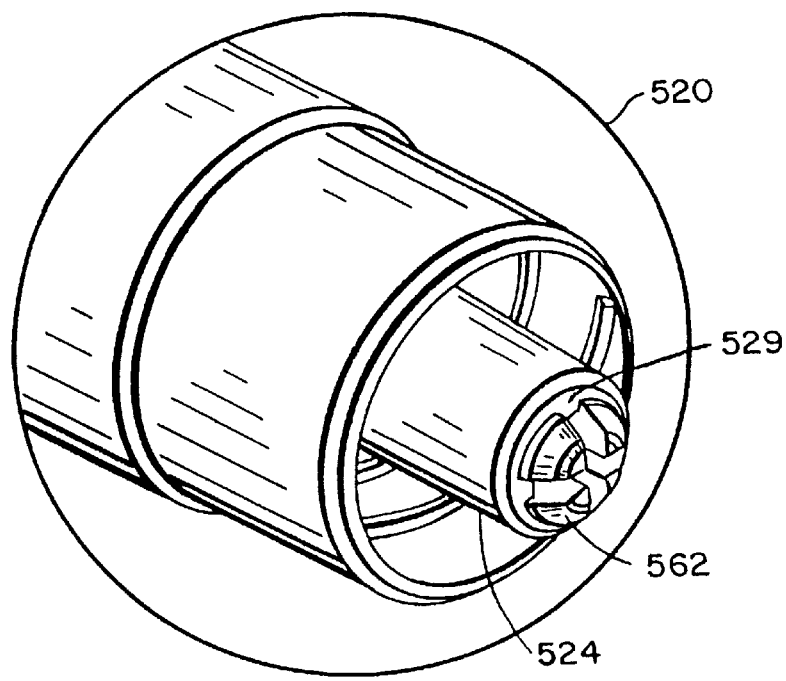
FIGS. 14 and 14A are isometric and cross-sectional views of the distal end of a sixth embodiment of the present invention with the plunger in the locked position.
Figure 14A:
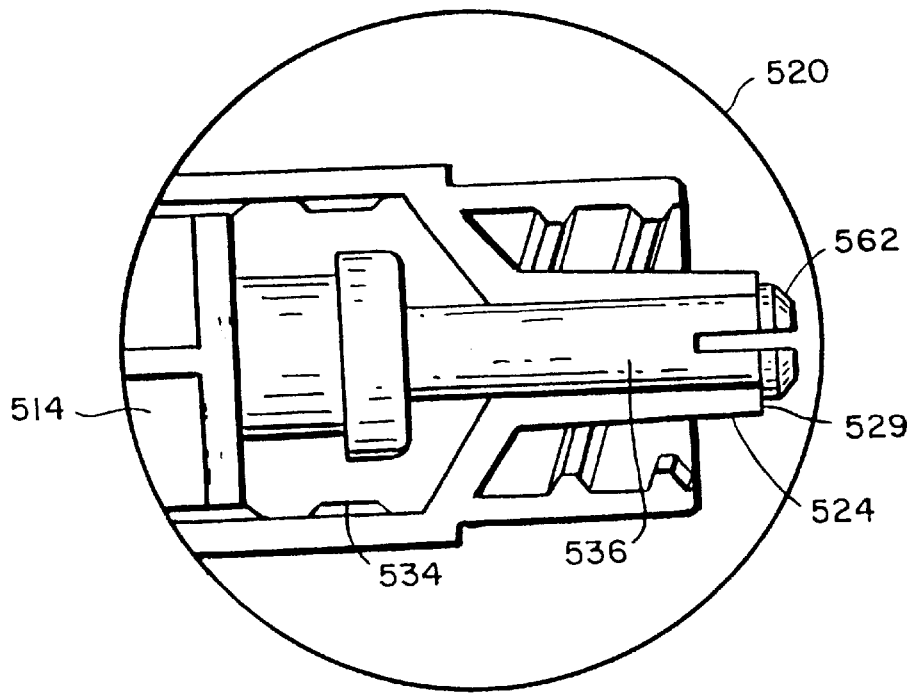

FIGS. 12 and 12A illustrate this embodiment with the plunger tip 536 partially placed into nozzle 524. FIGS. 13 and 13A illustrate the embodiment where the plunger tip 536 has almost complete traveled through the nozzle 524. In this position the piston member 534 may be sized, as a design choice, to require compression for additional plunger assembly travel. FIGS. 14 and 14A illustrate the plunger assembly 514 in the locked state. As illustrated, plunger tip cap 562 has expanded out over the outer lip 529 of nozzle 524, thus locking the plunger assembly 514 into position inside pre-existing barrel 512. FIG. 15 illustrates the complete syringe assembly 500 in the locked position.

It will be understood by one of ordinary skill in the art that certain variations for plunger assembly 514, illustrated in FIG. 14A, are possible. For example, the embodiment illustrated has the plunger tip 536 furcated into four equal portions, but other designs are not so restricted and may furcate into different number of sections which may or may not be equal. In addition, the plunger assembly 514 is illustrated with an elastomeric piston member 534, but is not so restricted.

It should be understood that other embodiments of the present invention could be created with variations in shape, size and materials without departing from the spirit of the invention. Although the present invention has been described in detail with reference only to present preferred embodiments, it will be appreciated by one of ordinary skill in the art that various modifications can be made without departing from the invention. Thus, while a barrel and plunger with piston have been illustrated, other means for controllably retaining a volume via an actuating means are within the principles of this invention. In addition, while a locking plunger tip cap has been illustrated, other means for locking are also within the spirit of the invention. Accordingly, the invention is limited only by the following claims.

What is claimed is:

1. An apparatus comprising:
   a barrel having a first end, a second end, an internal surface and a longitudinal axis, said barrel first end having a cap portion at said barrel second end, said cap portion having an inner surface, an outer surface and a port connecting said inner surface to said outer surface;
   a piston having a cross section adapted to substantially conform to said barrel internal surface and central channel;
   a plunger in communication with a piston, said plunger adapted to move said piston along said barrel longitudinal axis between said barrel first end and said barrel second end; and
   a locking mechanism in communication with said plunger and adapted to pass through said piston central channel and extend beyond said piston, said locking mechanism further adapted to pass into said port and engage said port, whereby said piston is locked when said plunger is moved to said barrel second end.

2. The apparatus of claim 1 wherein said locking mechanism comprises a pin having a first and second end, said pin second end having at least one furcation and said pin first end in communication with said plunger.

3. The apparatus of claim 1 wherein said port further comprises an annular ring disposed within said port and biased toward said longitudinal axis and adapted to engage said at least one furcation.

4. The apparatus of claim 3 wherein said annular ring is further biased in a direction away from said barrel second end.

5. The apparatus of claim 1 or 2 wherein said piston comprises a compliant material adapted to conform to said barrel inner surface and to said locking mechanism.

6. The apparatus of claim 2, 3 or 4 where said at least one furcation comprises multiple furcations adapted to substantially surround said pin second end.

7. The apparatus of claim 6 wherein said annular ring is disposed substantially at said port second end.

8. The apparatus of claim 7 wherein said port further comprises means for means for mounting a hypodermic needle.

9. The apparatus of claim 1 wherein said locking mechanism comprises a pin having a first and second end, said pin second end having at least one detent and said pin first end in communication with said plunger.

10. The apparatus of claim 9 wherein said port further comprises an annular ring disposed within said port biased toward said longitudinal axis and adapted to engage said at least one detent.

11. The apparatus of claim 10 wherein said annular ring is further biased in a direction away from said barrel second end.

12. The apparatus of claim 9 or 10 wherein said piston comprises a compliant material adapted to conform to said barrel inner surface and to said locking mechanism.

13. The apparatus of claim 9, 10 or 11 where said at least one detent is adapted to substantially surround said pin second end.

14. The apparatus of claim 13 wherein said annular ring is disposed substantially at said port second end.

15. The apparatus of claim 14 wherein said port further comprises means for means for mounting a hypodermic needle.

16. An apparatus comprising:
   a barrel having a first end, a second end, an internal surface and a longitudinal axis, said barrel first end having a cap portion having an inner surface, an outer surface and a port connecting said inner surface to said outer surface;
   a piston having a cross section adapted to substantially conform to said barrel internal surface and a central channel;
   a plunger in communication with said piston, said plunger adapted to move said piston along said barrel longitudinal axis between said barrel first end and said barrel second end;
   a nozzle disposed on said port and having a first end and a second end with said nozzle disposed on said port at said nozzle first end, said nozzle further having a channel connecting said nozzle first end to said nozzle second end and adapted to allow the evacuation of said barrel; and
   a locking mechanism in communication with said plunger and adapted to pass through said piston central channel and extend beyond said piston, said locking mechanism further adapted to pass into and substantially occupy said nozzle, said locking mechanism further adapted to engage said nozzle, whereby said piston is locked when said plunger is moved to said barrel second end.

17. The apparatus of claim 16 wherein said locking mechanism comprises a pin having a first and second end, said pin second end having at least one detent and said pin first end in communication with said plunger.

18. The apparatus of claim 17 wherein said nozzle further comprises an annular ring disposed within said port and biased toward said longitudinal axis and adapted to engage said at least one detent.

19. The apparatus of claim 18 wherein said annular ring is further biased in a direction away from said barrel second end.

20. The apparatus of claim 17 or 18 wherein said piston comprises a compliant material adapted to conform to said barrel inner surface and to said locking mechanism.

21. The apparatus of claim 17, 18 or 19 where said at least lone detent is adapted to substantially surround said pin second end.

22. The apparatus of claim 21 wherein said annular ring is disposed substantially at said nozzle second end.

23. The apparatus of claim 22 wherein said nozzle further comprises means for mounting a hypodermic needle.

24. In a syringe having a plunger, a barrel and a port, the improvement comprising a locking mechanism in communication with said plunger and adapted to substantially occupy said port.

25. The syringe of claim 24 wherein said locking mechanism requires a change in force applied to said plunger upon initial engagement.

26. The apparatus of claim 7, 14, 22 or 24 wherein said locking mechanism requires a change in force applied to said plunger upon initial engagement.

27. The syringe of claim 24 wherein said locking mechanism is further adapted to provide an audible response upon locking.

28. The apparatus of 7, 14, 22 or 24 wherein said locking mechanism is further adapted to provide an audible response upon locking.

29. The syringe of claim 24 wherein said locking mechanism is further adapted to provide a tactile response upon locking.

30. The apparatus of claim 7, 14, 22 or 24 wherein said locking mechanism is further adapted to provide a tactile response upon locking.

31. The syringe of claim 25, 27 or 29 wherein said locking mechanism comprising a locking pin having a detent and said port having a locking ring, said locking ring adapted to engage said detent and retain said locking pin within said port.

32. In a syringe for delivering a therapeutic agent, the syringe having a plunger, a barrel and a port, the improvement comprising a displacement mechanism in communication with the plunger and adapted to substantially occupy said port when said plunger is depressed, whereby substantially all of the therapeutic agent is evacuated from the syringe and port.

33. The syringe of claim 32 wherein the nozzle further comprises a channel for delivery of the therapeutic agent and said displacement mechanism comprises a pin adapted to conform to the shape of said nozzle channel, whereby substantially all of the therapeutic agent is evacuated from the channel.

34. The syringe of claim 33 wherein said nozzle further comprises an outlet disposed on an end opposite said plunger and on an axis parallel to an axis of motion of the plunger.

35. The syringe of claim 34 wherein said pin of said displacement mechanism extends beyond said outlet when the plunger is placed at the nozzle end of the barrel.

36. The syringe of claim 35 further comprises means for engaging a hypodermic needle mounted on a receptacle, said receptacle adapted to allow said channel to communicate with the receptacle, whereby substantially all of the therapeutic agent is evacuated from said receptacle.

* * * * *